United States Patent [19]

Sera et al.

[11] 4,268,623

[45] May 19, 1981

[54] PHOTOGRAPHIC LIGHT-SENSITIVE MATERIAL HAVING A CARBOXYLIC ACID POLYMER ANTISTATIC LAYER

[75] Inventors: Hidefumi Sera; Kiyotaka Hori; Naohiko Sugimoto, all of Minami-ashigara, Japan

[73] Assignee: Fuji Photo Film Co., Ltd., Minami-ashigara, Japan

[21] Appl. No.: 111,498

[22] Filed: Jan. 11, 1980

[30] Foreign Application Priority Data

Jan. 11, 1979 [JP] Japan .................................... 54-1930

[51] Int. Cl.³ .............................................. G03C 1/78
[52] U.S. Cl. ..................................... 430/529; 430/631
[58] Field of Search ................................. 430/529, 631

[56] References Cited

U.S. PATENT DOCUMENTS

| | | | |
|---|---|---|---|
| 2,725,297 | 11/1955 | Morey ................................. | 430/529 |
| 3,062,649 | 11/1962 | Galminen et al. .................. | 430/529 |
| 3,573,083 | 3/1971 | Oshibuchi et al. .................. | 430/529 |
| 3,791,831 | 2/1974 | Bonin et al. ......................... | 430/529 |

FOREIGN PATENT DOCUMENTS 1496027 12/1977 United Kingdom .

*Primary Examiner*—Jack P. Brammer
*Attorney, Agent, or Firm*—Sughrue, Rothwell, Mion, Zinn and Macpeak

[57] ABSTRACT

A photographic light-sensitive material having an antistatic layer containing a water-soluble, film-forming polymer having a carboxylic acid group and gelatin, said layer further containing a carboxylic acid activating condensing agent.

14 Claims, No Drawings

PHOTOGRAPHIC LIGHT-SENSITIVE MATERIAL HAVING A CARBOXYLIC ACID POLYMER ANTISTATIC LAYER

BACKGROUND OF THE INVENTION

1. Field of the Invention

This invention relates to a photographic sensitive material, more particularly, to a photographic sensitive material having an antistatic layer containing not only a carboxylic acid polymer but also a carboxylic acid activating condensing agent that acts on the polymer to add appreciably to the physical strength of the antistatic layer.

2. Description of the Prior Art

Static buildup on photographic sensitive materials has long annoyed the photographic industry. Static electricity is generated during the manufacture and use of photosensitive materials when they are wound on rolls, rewound therefrom, transported on rollers or when they contact other objects in transit. Generation and accumulation of static charges is a product of, for example, the electric conductivity and triboelectric series of the photographic material, moisture, the properties of the contacted object as well as the atmosphere in which the contact occurs. Accumulated static electricity sometimes discharges to cause irregular fogging of the photosensitive material. This is so deleterious to the material that it may even lose its commercial value. For instance, an X-ray film, even if it experiences the slightest fogging, not only fails to achieve the intended purpose but may result in an inaccurate diagnosis.

It is well known to provide an antistatic layer in a photographic material so as to avoid any adverse effect of static buildup and many types of photographic materials have been proposed that incorporate an antistatic layer that dissipates static charges. Illustrative examples include U.S. Pat. Nos. 2,649,374, 3,033,679, 3,437,487, 3,525,621, 3,630,740, and 3,681,070. These references describe various antistats and antistatic layers that contain them. However, all these conventional antistatic agents or antistatic layers have serious defects that make them unsuitable for use as a component of a photographic sensitive material. For example, due to their poor function, they are unable to prevent fogging from occurring in a high-sensitivity photographic material, or the antistatic layer may dissolve in a developing bath to form scum, or the layer or the photographic material that contains it is so low in strength that it becomes less abrasion-resistant or durable until it is no longer of value as a commercial product or may cause troubles in the production line.

British Pat. No. 1,496,027 proposes an improved antistatic layer free from these defects which comprises (a) a water-soluble, film-forming anionic high molecular electrolyte in the form of a free acid (e.g., polystyrenesulfonic acid), (b) a film-forming, water-soluble, crosslinkable high molecular binder (e.g., polyvinyl alcohol) and (c) a cross-linking agent for said high molecular binder (e.g., glyoxal). However, the antistatic layer of this patent is such that it fixes the water-soluble, electrically conductive, anionic high molecular electrolyte within the network structure formed by the binder and the cross-linking agent therefor, and as a result, it cannot prevent dissolution of the electrolyte in a developing bath which unavoidably leads to a low pH and scum formation. In addition, the anionic electrolyte accounts for about a third to half the weight of the antistatic layer. In other words, a third to half of the antistatic film is not crosslinked and this insufficiency in the physical strength of the film poses a serious problem in the high-speed production of photographic light-sensitive materials.

SUMMARY OF THE INVENTION

As a result of extensive studies, it has been found that a photographic material containing an antistatic layer of the following composition is free from the defects of conventional products: (a) gelatin, (b) a film-forming, water-soluble polymer containing a carboxylic acid group (the polymer will hereunder be referred to as a carboxylic acid polymer), and (c) a carboxylic acid activating condensing agent.

The photographic light-sensitive material containing an antistatic layer of the above composition is far more effective in minimizing the adverse effect of static charges than the photographic system having the conventionally proposed antistatic layers. More importantly, it achieves a great improvement in the physical strength of the film that has been so low with the conventional proposals that their use has been limited. It increases remarkably the resistance of a photographic material in a processing bath (i.e., solvent resistance, abrasion resistance and heat resistance) as well as the resistance to wear by transport rollers in the manufacturing process. While the mechanism for the improvement achieved by this invention is not completely defined, the most likely explanation appears to be that the carboxylic acid polymer is acted upon by the carboxylic acid activating condensing agent to make the carboxylic acid polymer bond with gelatin, and as a consequence there is less unbound substance to be dissolved and the degree of cross-linking is increased.

DETAILED DESCRIPTION OF THE INVENTION

There is no particular limitation on the carboxylic acid polymer used in this invention and homopolymers or copolymers of vinyl monomers having a carboxyl group are used to advantage. Illustrative preferred vinyl monomers having a carboxyl group include acrylic acid, methacrylic acid, maleic anhydride (maleic acid, half esters, half amides, and other derivatives thereof), cinnamic acid, crotonic acid, citraconic acid, p-carboxystyrene, and vinyl-α-carboxymethyl ether. Preferred vinyl monomer having a carboxyl group can be represented as:

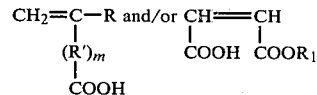

wherein R' is a phenylene group, R is a hydrogen atom or a methyl group and $R_1$ is a hydrogen atom or an alkyl group having 1 to 5 carbon atoms, and m is 0 or 1, preferably m is 0.

Illustrative monomers copolymerizable with the vinyl monomers having a carboxyl group include ethylenic unsaturated monomers such as ethylene, vinyl acetate, styrene, alkyl vinyl ethers such as methyl vinyl ether, acrylate esters (such as ethyl acrylate, butyl acrylate and phenyl acrylate), methacrylate esters (such as ethyl methacrylate, butyl methacrylate and phenyl methacrylate), acrylamide derivatives such as acrylamide acryloyl morpholine, methacrylamide and their derivatives, and vinylpyrrolidone. For the purpose of increasing the physical strength of the antistatic layer, the vinyl monomers may be copolymerized with monomers having a hydroxyl group such as hydroxyethyl acrylate, hydroxyethyl methacrylate and hydroxypropyl acrylate, or monomers having a functional group such as chloromethylstyrene, acetoacetoxyethyl methacrylate and glycidyl acrylate.

The carboxylic acid polymer used in this invention is required to have a molecular weight sufficient to provide a strong cross-linked film. The molecular weight differs from polymer to polymer but it is generally within the range of from about 5,000 to 500,000, preferably from about 10,000 to 200,000. The carboxylic acid polymer that can be used with advantage in this invention has the following base unit:

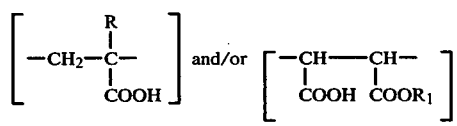

wherein R is a hydrogen atom or a methyl group, and $R_1$ is a hydrogen atom or an alkyl group having 1 to 5 carbon atoms. The vinyl monomer having a carboxyl group can be present in an amount of 30 to 100 mol%. Illustrative polymeric acids that can be used advantageously in this invention are given below by reference to their base units:

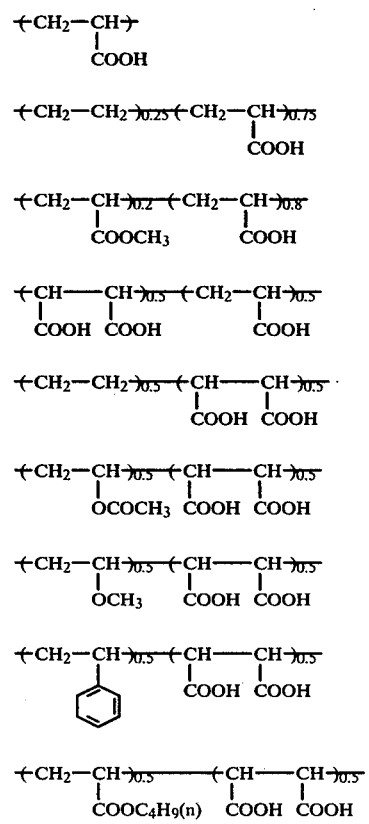

The carboxylic acid activating condensing agent used in this invention is any reagent that has the ability to activate a carboxyl group so that it reacts with one molecule of alcohol or amine to cause dehydration or condensation. These reagents are well known in the art of peptide synthesis and include compounds such as N-ethyl-5-phenylisoxazolium-3′-sulfonate (known as Woodward's Reagent K), N-tert-butyl-5-methylisoxazolium perchlorate (known as Woodward's Reagent L), isoxazolium salts of the type described in U.S. Pat. Nos. 3,543,292, 3,060,028, 3,316,095, 3,321,313, and 3,543,292, N,N-dicyclohexylcarbodiimide (known as DCC), as a water-soluble version 1-ethyl-3-(3-dimethylaminopropyl)carbodiimide hydrochloride, and carbodiimides, dihydroquinoline-N-carboxylate esters, carbamoyl pyridinium salts, carbamoyl oxypyridinium salts and 6-chloro-1-p-chlorobenzenesulfonyloxy benzotriazole of the type described in U.S. Pat. No. 3,619,236 and Japanese Patent Publication No. 38715/71.

The compounds of the following formulae (I) to (III) are particularly preferred as the activating condensing agent used in the present invention.

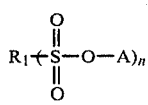  (I)

$R_1$ may be any n-valent group and is preferably a substituted or unsubstituted hydrocarbon having 1 to 10 carbon atoms. The hydrocarbon may be straight chained, branched or cyclic and may be saturated or unsaturated. $R_1$ is preferably an alkyl, alkylene, aryl, arylene or vinyl group having 1 to 7 carbon atoms. Illustrative substituents for $R_1$ include an alkoxy group having up to 4 carbon atoms (e.g., methoxy or ethoxy), an acyloxy group having up to 7 carbon atoms (e.g., acetoxy), a carboxylic acid amido group having up to 7 carbon atoms, an alkyloxy carbonyl group having up to 7 carbon atoms, a halogen atom (e.g., chlorine or bromine), a quaternary ammonium group, a tertiary amino group and salts thereof. An alkoxy group having up to 4 carbon atoms is a preferred substituent for $R_1$.

A represents a group of atoms that are bound to the oxygen atom (in the formula (I)) through a nitrogen atom, and it is preferably represented by the following formula (I'):

  (I')

wherein $B_1$ and $B_2$ are independently a hydrogen atom, an alkyl group (particularly having up to 7 carbon atoms) and an acyl group (including aliphatic, aromatic, sulfonic acyl groups, etc., particularly having up to 7 carbon atoms), provided that at least one of $B_1$ and $B_2$ is an acyl group; $B_1$ and $B_2$ may combine to form a 5- or 6-membered ring; illustrative 5- or 6-membered rings are:

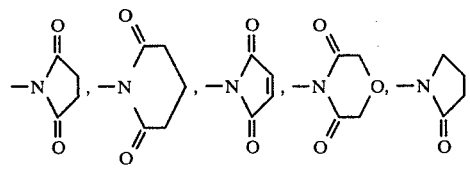

or they may form condensed rings of the following formulae:

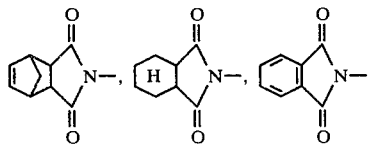

n is an integer of from 1 to 4 with n=1 being particularly preferred.

The compound of the formula (I) can be synthesized in high yield by common methods, for example, by reacting the corresponding n-valent sulfonic acid halide with the corresponding N-hydroxy compound in an organic solvent or aqueous solution in the presence of an organic base such as triethylamine, pyridine, or 1,4-diazobicyclo[2,2,2]undecene, or a dehydrohalogenating agent such as sodium carbonate or sodium hydroxide. The n-valent sulfonic acid halide (mainly sulfonic acid chloride) is in almost all cases derived from the corresponding sulfonic acid or salts thereof. These n-valent sulfonic acids (or salts thereof) are well known in the art, and they include monovalent sulfonic acids such as methanesulfonic acid, ethanesulfonic acid, propanesulfonic acid, γ-chloropropanesulfonic acid, γ-methoxypropanesulfonic acid, γ-ethoxypropanesulfonic acid, δ-methoxybutanesulfonic acid, β-carbamoylethanesulfonic acid, p-chlorobenzenesulfonic acid, p-nitrobenzenesulfonic acid, m-carbamoylbenzenesulfonic acid; and di- or trivalent sulfonic acids such as methionic acid, 1,2-ethanedisulfonic acid, 1,3-propanedisulfonic acid, 1,4-butanedisulfonic acid, 1,3-butanedisulfonic acid, 2-methyl-1,4-butanedisulfonic acid, and 3-oxa-1,5-pentanedisulfonic acid. The other starting material, the N-hydroxy compound, is exemplified by N-hydroxysuccinimide, N-hydroxyglutarimide, N-hydroxymaleinimide, N-hydroxymethylsuccinimide, N-hydroxymethoxysuccinimide, and N-hydroxyglycolimide.

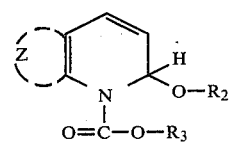  (II)

wherein $R_2$ represents any group that can be removed from the quinoline nucleus as an $R_2-O^\ominus$ group, $R_3$ represents a substituted or unsubstituted aliphatic group or an aryl group and Z represents the atoms necessary to form a substituted or unsubstituted benzene ring.

$R_2$ may be any group that can be removed from the quinoline nucleus of the formula (II) as $R_2-O^\ominus$. $R_2$ is, for example, an aliphatic group such as an unsubstituted alkyl group which may be straight or branched chained or cyclic and preferably has up to 6 carbon atoms (e.g., methyl, ethyl, propyl, butyl, etc.) or a substituted alkyl group (illustrative substituents are an alkoxy group such as methoxy or ethoxy; an alkylamino group such as dimethylamino; halogen atoms such as chlorine; and an aryl group).

$R_3$ is an aliphatic group such as an unsubstituted alkyl group (which may be straight or branched chained or cyclic and preferably has up to 6 carbon atoms, for example, methyl, ethyl, propyl or butyl) or a substituted alkyl group (illustrative substituents are an alkoxy group such as methoxy or ethoxy; an alkylamino group such as dimethylamino; and an aryl group having 6 to 7 carbon atoms), or a mono- or bicyclic aryl group having 6 to 12 carbon atoms. The carboxylic acid residue of the formula $R_3-O-CO-$ in the formula (II) is such that when it reacts with the carboxylic acid group of gelatin to form a mixed acid anhydride, the electron density on the carbon atom of the carbonyl group is lower than that of the carboxylic acid group in gelatin.

Z represents a group of atoms necessary to form a benzene nucleus (wherein the benzene nucleus may be substituted with an alkyl group such as a methyl or ethyl group or a halogen atom such as a bromine atom).

The aryl group (e.g., phenyl group) represented by $R_2$ or $R_3$ may be substituted with a substituent which is preferably free from a reactive hydrogen atom. Effective substituents include a nitro group, a halogen atom such as chlorine or bromine, an alkoxy group such as a methoxy or ethoxy group, and a dialkylamino group such as a dimethylamino group.

Some compounds of the formula (II) of this invention are commercially available, but the compounds of the formula (II) are generally synthesized with ease, and no cases have been reported of their deleterious effect on humans, and what is more, they are not only stable per se but they are also very stable as a solution (e.g., in methyl alcohol).

$$
\begin{array}{c}
R_6 \\
\phantom{x} \\
R_7
\end{array}
N-\underset{Y}{\overset{R_8}{C}}-W-\overset{\oplus}{N}\begin{array}{c}R_9\\ \\ R_{10}\end{array}\quad X^{\ominus} \quad (III)
$$

$R_6$ and $R_7$ are independently an alkyl, allyl or aralkyl group which preferably have 1 to 7 carbon atoms; $R_6$ and $R_7$ may combine to form a 5- or 6-membered ring which may contain 1 to 2 hetero atoms (such as nitrogen, oxygen or sulfur) other than the nitrogen atom to which $R_6$ and $R_7$ are bound.

Y is an oxygen atom or sulfur atom, and an oxygen atom is preferred.

W is an oxygen atom or is a single bond.

$R_8$, $R_9$ and $R_{10}$ are independently a hydrogen atom, an alkyl group having up to 5 carbon atoms, an alkoxy group having up to 4 carbon atoms, an acylamido group having up to 4 carbon atoms, and a carbamoyl group which may be, e.g., an alkylcarbamoyl group having up to 7 carbon atoms.

$X^{\ominus}$ is an organic or inorganic acid anion and is preferably a halogen ion such as Cl or Br, a sulfate ion or organic sulfonate ion (such as methanesulfonate, benzenesulfonate, toluenesulfonate, etc.); $X^{\ominus}$ is absent from the formula (III) when either one of $R_6$, $R_7$, $R_8$, $R_9$ and $R_{10}$ is a sulfonate anion.

The compound of the formula (III) can be synthesized by the method disclosed in West German Patent Application (OLS) No. 2,408,814 when W is an oxygen atom, and can be synthesized by the method of West German Patent Application (OLS) No. 2,408,813 when W is simply a bond.

Representative compounds of the formulae (I) to (III) are illustrated below but these examples in no way limit the present invention. In general, compounds of the formula (I) are favored over compounds of the formula (II) which are favored over compounds of the formula (III).

-continued

Compound-13

[structure: carbamate of tetrahydroquinoline with O—CH₂CH₂—O—CH₃ and O=C—O—C₂H₅]

Compound-14

[structure: tetrahydroquinoline with O—CH₃ and O=C—O—CH₂CH(CH₃)₂]

Compound-15

[structure: tetrahydroquinoline with O—CH₂CH(CH₃)₂ and O=C—O—CH₂CH(CH₃)₂]

Compound-16

[structure: tetrahydroquinoline with O—CH₂CH₂—N(CH₃)₂ and O=C—O—C₂H₅]

Compound-17

(CH₃)₂N—CO—⊕N(pyridinium-SO₃⁻)  Na⊕Cl⊖

Compound-18

(morpholino)N—CO—⊕N(pyridinium-SO₃⁻)  Na⊕Cl⊖

Compound-19

(CH₃)₂N—C(=O)—⊕N(pyridinium)  Cl⊖

Compound-20

(morpholino)N—C(=O)—⊕N(pyridinium-CONH₂)  Cl⊖

Compound-21

(CH₃)₂N—C(=O)—O—⊕N(pyridinium)  Cl⊖

Compound-22

(C₂H₅)₂N—C(=O)—O—⊕N(pyridinium-CH₃)  ClO₄⊖

Compound-23

(piperidino)N—C(=O)—O—⊕N(pyridinium)  Cl⊖

The following are illustrative methods of synthesizing the carboxylic acid activating condensing agent of this invention.

SYNTHESIS EXAMPLE 1

Synthesis of Compound-1

A solution of 5 g of ethanesulfonyl chloride in 20 ml of dried acetone was added dropwise to 4.6 g of N-hydroxysuccinimide in 80 ml of dried acetone with cooling. At a temperature lower than 0° C., 4 g of triethylamine in 20 ml of acetone was added dropwise to the mixture under stirring which continued for a period of 3 hours. Following stirring for another 2 hours at room temperature, the mixture was filtered by means of suction, the filtrate was concentrated under vacuum, 300 ml of ice water was added, and the resulting white crystal was filtered off and dried to provide 7.5 g of a white needle-like crystal having a melting point of 140° C.

| Elemental Analysis | C | H | N |
|---|---|---|---|
| Calculated (%): | 34.78 | 4.35 | 6.76 |
| Found (%): | 34.56 | 4.42 | 6.77 |

SYNTHESIS EXAMPLE 2

Synthesis of Compound-2

N-hydroxysuccinimide was reaced with γ-methoxypropanesulfonyl chloride in the same manner as in Synthesis Example 1. A white crystal having a melting point of 75° to 76° C. was obtained.

SYNTHESIS EXAMPLE 3

Synthesis of Compound-12

Ethyl chloroformate (97 ml) was added to a solution of 130 g of quinoline in 300 ml of benzene under cooling. The solution was further cooled to −5° C., and a solution of 155 ml of triethylamine in 92 ml of ethyl alcohol was added dropwise under stirring which continued for a period of 1 hour. The mixture was washed with water, the aqueous layer was extracted with chloroform and concentrated under vacuum together with the oily layer. About 20 cc of ethyl ether was added to the residue and then it was crystallized. The crystal was filtered off. Yield: 165 g (66%); Melting point: 63.5° to 65° C.

SYNTHESIS EXAMPLE 4

Synthesis of Compound-13

The procedure of Synthesis Example 3 was repeated to perform a reaction using quinoline, ethyl chloroformate, triethylamine and ethylene glycol monomethyl ether. The reaction mixture was washed with a small amount of water and distilled under vacuum. Fractions (160°–162° C. at 0.6 mmHg) were combined. Yield: 56%

SYNTHESIS EXAMPLE 5

Synthesis of Compound-18

The procedure described in U.S. Pat. No. 4,063,952 was repeated to provide a crystal having a melting point of 236° to 237° C.

SYNTHESIS EXAMPLE 6

Synthesis of Compound-21

The procedure described in U.S. Pat. No. 4,055,427 was repeated to provide a solid product having a melting point of 162° to 166° C. (with decomposition).

The thus prepared carboxylic acid activating condensing agent is added to the carboxylic acid polymer in an amount of about 0.01 to 50 millimols, preferably from 0.5 to 20 millimols, per mol of the carboxylic acid group.

The condensing agent may be incorporated in the layer of the carboxylic acid polymer. Alternatively, it may be incorporated in a layer adjacent to the layer of the polymer (e.g., a photographic emulsion layer, an emulsion protective layer, an intermediate layer, a subbing layer, an antihalation coating, a filter layer, or a back protective layer) such that it diffuses to the polymer layer.

The carboxylic acid polymer of this invention may optionally be neutralized with alkali. The alkali includes alkaline earth metals, alkali metals and organic bases, and sodium, potassium and lithium hydroxides are preferred. There is no particular limitation on the degree of neutralization, and preferably about 5 to 60 mol% of the carboxylic acid group is neutralized to give a pH of an aqueous solution of the polymer in the range of about 5.0 to 7.5. According to this invention, the carboxylic acid polymer is incorporated in the antistatic layer in an amount of from about 10 wt% to 90 wt%, preferably about 20 wt% to 70 wt%, of the antistatic layer.

The antistatic layer of this invention may contain any conventional type gelatin, i.e., alkali-treated gelatin, acid-treated gelatin and enzyme-treated gelatin, and acid-treated gelatin is preferred. The antistatic layer contains about 10 to 90 wt%, preferably about 20 to 70 wt%, of gelatin.

There is no particular limitation on the thickness of the antistatic layer but it is generally about 0.5 to 20 microns thick, and preferably about 3 to 10 microns thick.

The antistatic layer of this invention may also contain a matting agent, a lubricant, a surfactant, a colloidal silica, and a gelatin cross-linking agent other than the condensing agent defined herein. A suitable matting agent is beads (about 0.1 to 10 microns in size) of silica (silicon dioxide), polymethyl methacrylate, barium sulfate, titanium dioxide, polyolefin, etc.

Illustrative surfactants include nonionic surfactants such as saponin (steroid type), alkylene oxide derivatives (such as polyethylene glycol, polyethylene glycol/polypropylene glycol condensate, polyethylene glycol alkyl or alkylaryl ether, polyethylene glycol ester, polyethylene glycol sorbitan ester, polyalkylene glycol alkylamine or amide, and silicone/polyethylene oxide adduct), glycidol derivatives (such as alkenylsuccinic acid polyglyceride and alkylphenol polyglyceride), aliphatic acid esters of polyols, and alkyl esters, urethanes and ethers of saccharides; anionic surfactants containing acidic groups such as a carboxyl group, a sulfo group, a phospho group, a sulfate ester group and a phosphate ester group, such as triterpenoidsaponin, alkyl carboxylate salts, alkyl sulfonate salts, alkylbenzenesulfonate salts, alkylnaphthalenesulfonate salts, alkylsulfate esters, alkylphosphate esters, N-acyl-N-alkyltaurines, sulfosuccinate esters, sulfoalkylpolyoxyethylene alkylphenyl ethers and polyoxyethylene alkylphosphate esters; amphoteric surfactants such as amino acids, aminoalkyl sulfonic acids, aminoalkyl sulfate and phosphate esters, alkylbetaines, amine imides, and amine oxides; cationic surfactants such as alkyl amine salts, aliphatic or aromatic quaternary ammonium salts, heterocyclic quaternary ammonium salts such as pyridinium and imidazolium, and phosphonium and sulfonium salts containing an aliphatic group or heterocyclic ring; and fluorine-containing surfactants (anionic, nonionic, cationic and betaine-type).

Specific examples of these surfactants are described in U.S. Pat. Nos. 2,240,472, 2,831,766, 3,158,484, 3,210,191, 3,294,540, 3,507,660, 2,739,891, 2,823,123, 3,068,101, 3,415,649, 3,666,478, 3,756,828, 3,133,816, 3,441,413, 3,475,174, 3,545,974, 3,726,683, 3,843,368, 2,271,623, 2,288,266, 2,944,900, 3,253,919, 3,671,247, 3,722,021, 3,589,906, 3,666,478, 3,574,924, British Patents 1,012,495, 1,022,878, 1,179,290, 1,198,450, 1,397,218, 1,138,514, 1,159,825, 1,374,780, 1,570,961, 1,503,218, Belgian Pat. No. 731,126, West German Patent Application (OLS) No. 1,961,638, West German Patent Application No. 2,556,670, Japanese Patent Application (OPI) Nos. 117414/74, 59025/75, 21932/78, 77135/77 (The term "OPI" as used herein refers to a "published unexamined Japanese patent application").

Colloidal silica is commercially available as Ludox AM (manufactured by E. I. Du Pont) or SNOW Tex O (manufactured by Nissan Chemical Industries, Ltd.).

The antistatic layer of this invention may be coated by techniques conventionally used for application of aqueous coating compositions. These techniques include dip coating, air knife coating, curtain coating, spray coating and extrusion coating using a slide hopper. The antistatic layer can be applied to negative films, reversal fils and photographic paper for both color and black-and-white photography for the purpose of eliminating the adverse effect of static electricity.

Suitable supports for these photographic materials include cellulose acetate, cellulose nitrate, polyvinyl acetal, polycarbonate, polyester, polystyrene, and baryta paper as well as photographic paper coated with polystyrene, cellulose acetate, polyester and polyolefin.

The antistatic layer of this invention may be coated on a polyester film through a subbing layer which is provided to obtain intimate contact between the antistatic layer and the film. Various known techniques can be used without any particular limitation to provide an effective subbing layer. The antistatic layer of this invention can also be disposed at any location without particular limitation. For instance, the antistatic layer disposed on the back surface may be overlaid with a protective layer. Alternatively, the antistatic layer may form the outermost layer. When it is disposed on an emulsion layer, it may be so arranged adjacent to the subbing layer; alternatively, it may either form or be adjacent to the outermost surface protective layer. These arrangements may be combined to provide a plurality of antistatic layers. The antistatic layer of this invention preferably forms the back layer, the protective layer for the back layer, and/or the surface protective layer facing the sensitive emulsion layer.

The sensitive emulsion layer used in the photographic sensitive material of this invention will hereunder be described. Any type of conventional silver halides, i.e., silver chloride, silver bromide, silver bromoiodide, silver chlorobromide, silver chloroiodide, and silver chlorobromoiodide, may be used as the emulsion. These halides may be used independently or as a mixture. A hydrophilic colloid is generally selected as a binder. Typical examples of the colloid include protein such as gelatin and its derivatives, cellulose derivatives, starch, saccharides including polysaccharides such as dextran, vegetable rubber, and synthetic polymers such as polyvinyl alcohol, polyacrylamide and polyvinyl pyrrolidone. The photographic sensitive material of this invention may further contain conventional additives such as an antifoggant, photographic stabilizer, sensitizer, developer additives, curing agent, plasticizer, surfactant, color coupler and polymer latex. For details of these additives, reference may be had to *Product Licensing Index*, Vol. 92, pp. 107–110, December 1971.

This invention is now described in greater detail by reference to the following examples. It should of course be understood that the examples are given here for illustrative purposes only and that the scope of this invention is by no means limited thereto.

EXAMPLE 1

Five samples (1), (2), (3), (4) and (5) were prepared by conventional coating and drying techniques. Each sample had a back layer and its protective layer on one side of a cellulose triacetate support and had an antihalation coating, a red-sensitive layer, an intermediate layer, a green-sensitive layer, a yellow filter layer, a blue-sensitive layer and a protective layer superimposed on the opposite side of the back layer in that order. The composition of each layer was as follows.

Back Layer

Binder: gelatin 6.2 g/m²
Salt: potassium nitrate 0.1 g/m²
Hardener: bis(vinylsulfonylmethyl)ether 0.6 g/100 g binder Back Protective Layer Binder: gelatin 2.2 g/m²
Matting agent: polymethyl methacrylate (average particle size: 2.5μ) 20 mg/m²
Hardener: bis(vinylsulfonylmethyl)ether 1.2 g/100 g binder
Coating agent:

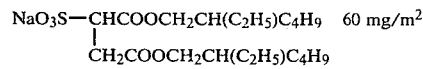
NaO₃S—CHCOOCH₂CH(C₂H₅)C₄H₉     60 mg/m²
         |
         CH₂COOCH₂CH(C₂H₅)C₄H₉

Antihalation Coating

Binder: gelatin 4.4 g/m²
Hardener: bis(vinylsulfonylmethyl)ether 5 g/100 g binder
Coating aid: sodium dodecylbenzenesulfonate 4 mg/m²
Antihalation agent: black colloidal silver 0.4 g/m²

Red-Sensitive Layer

Binder: gelatin 7 g/m²
Hardener: sodium salt of 2-hydroxy-4,6-dichloro-s-triazine 0.7 g/100 g binder + bis(vinylsulfonylmethyl)ether 2 g/100 g binder
Coating aid: sodium dodecylbenzenesulfonate 10 mg/m²
Weight of silver coat: 3.1 g/m²
Silver halide: AgI 2 L mol% + AgBr 98 mol%
Fog restrainer: 4-hydroxy-6-methyl-1,3,3a,7-tetrazaindene 0.9 g/Ag 100 g
Coupler: 1-hydroxy-4-(2-acetylphenyl)azo-N-[4-(2,4-di-tert-amylphenoxy)butyl]-2-naphthoamide 38 g/Ag 100 g
Sensitizing dye: pyridinium salt of anhydro-5,5'-dichloro-9-ethyl-3,3'-di(3-sulfopropyl)thiacarbocyaninehydroxide 0.3 g/Ag 100 g Intermediate Layer Binder: gelatin 2.6 g/m²
Hardener: bis(vinylsulfonylmethyl)ether 6 g/100 g binder
Coating aid: sodium dodecylbenzenesulfonate 12 mg/m²

Green-Sensitive Layer

Binder: gelatin 6.4 g/m²
Hardener: sodium salt of 2-hydroxy-4,6-dichloro-s-triazine 0.7 g/100 g binder + bis(vinylsulfonylmethyl)ether 2 g/100 g binder
Coating aid: sodium dodecylbenzenesulfonate 9 mg/m²
Weight of silver coat: 2.2 g/m²
Silver halide: AgI 3.3 mol% + AgBr 96.7 mol%
Stibilizer: 4-hydroxy-6-methyl-1,3,3a,7-tetrazaindene 0.6 g/Ag 100 g
Coupler: 1-(2,4,6-trichlorophenyl)-3-[3-(2,4-di-tert-amylphenoxy)acetamido]-4-(4-methoxyphenyl)azo-5-pyrazolone 37 g/Ag 100 g
Sensitizing dye: pyridinium salt of anhydro-5,5'-diphenyl-9-ethyl-3,3'-di(2-sulfoethyl)oxacarbocyanine hydroxide 0.3 g/Ag 100 g Yellow Filter Layer Binder: gelatin 2.3 g/m²
Filter: yellow colloidal silver 0.7 g/m²
Hardener: bis(vinylsulfonylmethyl)ether 5 g/100 g binder
Surfactant: sodium salt of bis(2-ethylhexyl)-2-sulfosuccinate 7 mg/m²

Blue-Sensitive Layer

Binder: gelatin 7 g/m²
Hardener: sodium salt of 2-hydroxy-4,6-dichloro-s-triazine 0.7 g/100 g binder + bis(vinylsulfonylmethyl)ether 2 g/100 g binder
Coating aid: sodium dodecylbenzenesulfonate 8 mg/m²
Weight of silver coat: 2.2 g/m²
Silver halide: AgI 3.3 mol% + AgBr 96.7 mol%
Stabilizer: 4-hydroxy-6-methyl-1,3,3a,7-tetrazaindene 0.4 g/Ag 100 g
Coupler: 2'-chloro-5'-[2-(2,4-di-tert-amylphenoxy)-butylamido]-α-(5,5'-dimethyl-2,4-dioxo-3-oxazolidinyl)-α-(4-methoxybenzoyl)-acetanilide 45 g/Ag 100 g Protective Layer Binder: gelatin 2 g/m² + styrene-maleic anhydride copolymer (1:1) having a molecular weight of abou 100,000 0.3 g/m²
Hardener: bis(vinylsulfonylmethyl)ether 5 g/100 g binder
Coating aid: sodium dioctylsulfosuccinate 5 mg/m²
Matting agent: silver halide mat (average particle size 2μ) 500 mg/m² as AgBr Sample (1) consisted only of the above components. Sample (2) was the same as Sample (1) except that its back layer contained 3.1 g/m² of Polymer-1 of this invention which was neutralized with sodium hydroxide to a pH of 7.0. Sample (3) was the same as Sample (1) except that its back layer contained 3.1 g/m² of Polymer-20 of this invention which was neutralized with sodium hydroxide to a pH of 7.1. Sample (4) was the same as Sample (2) except that its back layer contained 47 mg/m² of the carboxylic acid activating condensing agent of this invention, Compound-1. Sample (5) was the same as Sample (3) except that its back layer contained 93 mg/m² of the carboxylic acid activating condensing agent Compound-2. These samples were subjected to the following tests of antistatic property and film strength, the results of which are set forth in Table 1 below.

I. Determination of Antistatic Property (1) After moisture conditioning at 25° C. and 25% RH for 1 day, each test piece was placed between brass electrodes 10 cm long and 0.14 cm spaced apart (interface with test piece covered with stainless steel). After 100 volts D.C. was applied across the electrodes for 1 minute, the amperage was read on an electrometer (TR-8651 manufactured by Takeda Riken Industry Co., Ltd.), from which the surface resistivity was calculated. The smaller the surface resistivity, the more antistatic the test piece was.

(2) Formation of static marks

After moisture conditioning under the same conditions as (1), each test piece was passed through a pair of black rubber rolls under a load of 2.5 kg, developed photographically, and checked for any static marks.

II. Determination of Film Strength

Each test piece was immersed in a developer at 38° C. for 5 minutes and scratched with a 1 mm diameter sapphire stylus of a scratch tester which was able to apply a continuous load within the range of from 0 to 200 g. The film strength was determined as the value of the load which first gave a scratch on the test piece.

As Table 1 clearly indicates, the carboxylic acid polymer improved the antistatic property of the photographic material but it reduced the film strength considerably. The combination of gelatin, carboxylic acid polymer and the carboxylic acid activating condensing agent according to this invention could improve the antistatic property remarkably without reducing the film strength.

EXAMPLE 2

Sample (11) which was the same as Sample (1) of Example 1 was prepared. Samples (12), (13) and (14) were prepared which were the same as Sample (11) except that their back layers contained Polymer-4 and Condensing Agent Compound-4 of this invention in the amounts indicated in Table 2 below. These samples were subjected to the measurement of antistatic property and film strength in the same manner as in Example 1. The results are given in Table 2.

TABLE 2

| | Composition of Back Layer | | | Results | | |
|---|---|---|---|---|---|---|
| Sample No. | Gelatin (g/m²) | Carboxylic Acid Polymer | Activating Condensing Agent | Surface Resistivity (Ω) | Formation of Static Marks | Film Strength (g) |
| 11 | 6.2 | absent | absent | 13.5 | C | >200 |
| 12 (invention) | 6.2 | Polymer-4 0.6 g/m² | Compound-4 24 mg/m² | 12.5 | B | >200 |
| 13 (invention) | 6.2 | Polymer-4 2.0 g/m² | Compound-4 80 mg/m² | 11.6 | A | >200 |
| 14 (invention) | 6.2 | Polymer-4 6.2 g/m² | Compound-4 248 mg/m² | 10.1 | A | >200 |

As Table 2 shows, the combination of gelatin, the carboxylic acid polymer and carboxylic acid activating condensing agent of this invention improved the antistatic property of the photographic material and increased the film strength. Use of more than 20 wt% of the carboxylic acid polymer on the basis of the gelatin was particularly effective for improvement of the antistatic property.

EXAMPLE 3

Sample (21) which was the same as Sample (1) of Example 1 was prepared. Samples (22), (23), (24) and (25) were prepared which were the same as Sample (21) except that their back layer contained Polymer-19 50 mol% of which is neutralized with KOH and Condensing Agent Compound-7 of this invention in the amounts indicated in Table 3 below. These samples were subjected to the measurement of antistatic property and film strength in the same manner as in Example 1. The results are specified in Table 3.

TABLE 1

| | Composition of Back Layer | | | Results | | |
|---|---|---|---|---|---|---|
| Sample No. | Gelatin | Carboxylic Acid Polymer | Activating Condensing Agent | Surface Resistivity (Ω) | Formation* of Static Marks | Film Strength (g) |
| 1 | present | absent | absent | 13.5 | C | >200 |
| 2 | present | Polymer-1 | absent | 11.1 | A | 50 |
| 3 | present | Polymer-20 | absent | 11.3 | A | 50 |
| 4 (invention) | present | Polymer-1 | Compound-1 | 11.1 | A | >200 |
| 5 (invention) | present | Polymer-20 | Compound-2 | 11.3 | A | >200 |

*A: Formation of static marks was negligible. B: Formation of static marks was noticeable. C: Static marks were formed over substantially all the surface.

TABLE 3

| Sample No. | Composition of Back Layer | | | Results | | |
|---|---|---|---|---|---|---|
| | Gelatin (g/m$^2$) | Carboxylic Acid Polymer | Activating Condensing Agent | Surface Resistivity (Ω) | Formation of Static Marks | Film Strength (g) |
| 21 | 6.2 | absent | absent | 13.5 | C | >200 |
| 22 | 6.2 | Polymer-19 3.1 g/m$^2$ | absent | 11.1 | A | 50 |
| 23 (invention) | 6.2 | Polymer-19 3.1 g/m$^2$ | Compound-7 4 mg/m$^2$ | 11.2 | A | 100 |
| 24 (invention) | 6.2 | Polymer-19 3.1 g/m$^2$ | Compound-7 40 mg/m$^2$ | 11.2 | A | >200 |
| 25 (invention) | 6.2 | Polymer-19 3.1 g/m$^2$ | Compound-7 160 mg/m$^2$ | 11.2 | A | >200 |

As Table 3 demonstrates, the use of more than 0.5 millimol of the carboxylic acid activating condensing agent per mol of the carboxyl group of the carboxylic acid polymer resulted in great improvement in the antistatic property and film strength.

EXAMPLE 4

Sample (31) was prepared which was the same as Sample (1) of Example 1. Sample (32) was also prepared and this was the same as Sample (31) except that the composition of its back layer was as follows.

Back Layer

Binder: gelatin 2.0 g/m$^2$
Antistatic agent: Polymer-1 (neutralized with NaOH to a pH of 7.0) 4.2 g/m$^2$
Salt: potassium nitrate 0.1 g/m$^2$
Hardener: bis(vinylsulfonylmethyl)ether 0.6 g/100 g binder Sample (33) was prepared which was the same as Sample (32) except that its back layer also contained 0.2 g/m$^2$ of glyoxal. Sample (34) was the same as Sample (32) except that its back layer also contained 60 mg/m$^2$ of Compound-7 of this invention. Sample (35) was the same as Sample (34) except that the gelatin used as the binder for both the back layer and the back protective layer was replaced with polyvinyl alcohol (88% hydrolyzed). These samples were subjected to the measurement of antistatic property and film strength as in Example 1. In addition, checking was made to see if each sample was dissolved to form a scum in a processing solution. For this purpose, a laboratory scale developing machine (capacity: 1.7 liters of processing solution) was used to process about 20 m$^2$ of each sample under the color developing conditions specified in Example 1 of Japanese Patent Application (OPI) No. 70821/78 corresponding to West German Patent Application (OLS) No. 2,754,281, and any scum formed in the fixer was observed by the naked eye. The results are indicated in Table 4 below.

TABLE 4

| Sample No. | Composition of Back Layer | | | Results | | | |
|---|---|---|---|---|---|---|---|
| | Binder | Carboxylic Acid Polymer | Cross-Linking Agent | Surface Resistivity (Ω) | Formation of Static Marks | Film Strength (g) | Dissolution in Processing Solution |
| 31 | gelatin | absent | bis(vinylsulfonylmethyl)-ether | 13.5 | C | >200 | no dissolution |
| 32 | gelatin | Polymer-1 | bis(vinylsulfonylmethyl)-ether | 10.0 | A | 50 | dissolved |
| 33 | gelatin | Polymer-1 | bis(vinylsulfonylmethyl)-ether + glyoxal | 10.3 | A | >200 | dissolved |
| 34 (invention) | gelatin | Polymer-1 | bis(vinylsulfonylmethyl)-ether + Compound 7 | 10.2 | A | >200 | no dissolution |
| 35 | polyvinyl alcohol | Polymer-1 | bis(vinylsulfonylmethyl)-ether + Compound 7 | 10.2 | A | 100 | dissolved |

As Table 4 shows clearly, Sample (34) of this invention had good antistatic property and high film strength and was free from the formation of scum in the processing solution. Sample (33) using glyoxal in place of the carboxylic acid activating condensing agent provided good antistatic property and high film strength, but it dissolved in the processing solution to form a scum. Sample (35) using polyvinyl alcohol rather than gelatin was not only low in film strength but it also formed a scum.

EXAMPLE 5

Samples (41) to (45) were prepared by the conventional coating and drying techniques. Each sample comprised a protective layer, an emulsion layer, a polyethylene terephthalate film support, an emulsion layer and a protective layer which were superimposed in that order. The composition of each layer was as follows.

Emulsion Layer

Binder: gelatin 2.5 g/m$^2$
Weight of silver coat: 5 g/m$^2$
Silver halide: AgI 1.5 mol% + AgBr 98.5 mol%
Hardener: chromium alum 0.8 g/100 g binder
Fog restrainer: 1-phenyl-5-mercaptotetrazole 0.5 g/Ag 100 g Protective Layer Binder: gelatin 1.7 g/m$^2$
Hardener: sodium salt of 2-hydroxy-4,6-dichloro-s-triazine 0.4 g/100 g binder
Coating aid: sodium salt of N-oleoyl-N-methyltaurine 7 mg/m$^2$
Matting agent: polymethylmethacrylate (average particle size 5μ) 25 mg/m$^2$ Sample (41) consisted only of these components. Sample (42) was the same as Sample (41) except that the protective layer contained 1.2 g/m² of Polymer-1 60 mol% of which was neutralized with sodium hydroxide. Sample (43) was the same as Sample (41) except that the protective layer contained 2.0 g/m² of Polymer-2 40 mol% of which was neutralized with potassium hydroxide. Sample (44) was the same as sample (42) except that the protective layer contained 60 mg/m² of carboxylic acid activating condensing agent Compound-3. Sample (45) was the same as Sample (43) except that the protective layer contained 60 mg/m² of carboxylic acid activating condensing agent Compound-7. These samples were subjected to the measurement of antistatic activity and film strength as in Example 1, the results of which are shown in Table 5 below.

TABLE 5

| Sample No. | Composition of Back Layer | | | Results | | |
|---|---|---|---|---|---|---|
| | Gelatin (g/m²) | Carboxylic Acid Polymer | Activating Condensing Agent | Surface Resistivity (Ω) | Formation of Static Marks | Film* Strength (g) |
| 41 | 1.7 | absent | absent | 14.2 | C | >200 |
| 42 | " | Polymer-1 1.2 g/m² | absent | 11.3 | A | 50 |
| 43 | " | Polymer-2 2.0 g/m² | absent | 10.0 | A | 50 |
| 44 (invention) | " | Polymer-1 1.2 g/m² | Compound-3 60 mg/m² | 11.3 | A | >200 |
| 45 (invention) | " | Polymer-2 2.0 g/m² | Compound-7 60 mg/m² | 10.0 | A | >200 |

*After immersion in RD-111 developer (manufactured by Fuji Photo Film Co., Ltd.) at 35° C. for 25 seconds, each sample was subjected to scratch test using the scratch tester of Example 1.

As Table 5 shows clearly, Samples (44) and (45) that contained gelatin, the carboxylic acid polymer and the carboxylic acid activating condensing agent in the surface protective layer had very good antistatic property without any loss in the film strength.

While the invention has been described in detail and with reference to specific embodiments thereof, it will be apparent to one skilled in the art that various changes and modifications can be made therein without departing from the spirit and scope thereof.

What is claimed is:

1. A photographic material comprising a support, a light-sensitive silver halide emulsion layer, and an antistatic layer, said antistatic layer containing about 10% to 90% wt% of a water-soluble, film-forming polymer having a carboxylic acid group and about 10 to 90 wt% gelatin, and said layer further containing a carboxylic acid activating condensing agent having the ability to activate a carboxyl group such that it reacts with an alcohol or amine in a condensation reaction, said agent being selected from the group consisting of a compound of the formula (I):

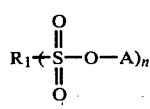

(I)

wherein R₁ may be any n-valent group; A represents a group of atoms that are bound to the oxygen atom in the formula (I) through a nitrogen atom; and n is an integer of from 1 to 4; a compound of the formula (II):

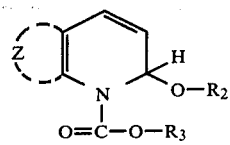

(II)

wherein R₂ is an aliphatic group; R₃ is an aliphatic group or an aryl group and the carboxylic acid residue of the formula R₃—O—CO— in the formula (II) is such that when it reacts with the carboxylic acid group of gelatin to form a mixed acid anhydride, the electron density on the carbonyl carbon is lower than that of the carboxylic acid group in gelatin; Z represents a group of atoms necessary to form a benzene nucleus, and a compound of the formula (III):

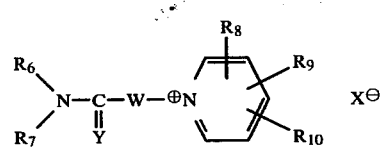

(III)

wherein R₆ and R₇ are independently an alkyl, allyl or aralkyl group and R₆ and R₇ may combine to form a 5- or 6-membered ring which may contain 1 to 2 hetero atoms other than the nitrogen atom to which R₆ and R₇ are bound; Y is an oxygen atom or sulfur atom; W is an oxygen atom or a single bond; R₈, R₉ and R₁₀ are independently a hydrogen atom, an alkyl group of up to 5 carbon atoms, an alkoxy group of up to 4 carbon atoms, an acrylamido group of up to 4 carbon atoms, and a carbamoyl group; X⊖ is an organic or inorganic acid anion, and X⊖ is absent from the formula (III) when any of R₆, R₇, Y, R₈, R₉ or R₁₀ includes a sulfonate anion.

2. The photographic material of claim 1, wherein said polymer having a carboxylic acid group has the following base unit:

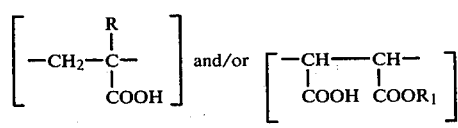

wherein R is a hydrogen atom or a methyl group; and R₁ is a hydrogen atom or an alkyl group having 1 to 5 carbon atoms.

3. The photographic material of claim 1, wherein the antistatic layer contains about 20 to 70 wt% of the carboxylic acid containing polymer.

4. The photographic material of claim 1, wherein the antistatic layer contains about 20 to 70 wt% of gelatin.

5. The photographic material of claim 1, wherein the carboxylic acid activating condensing agent is a compound of the formula (I):

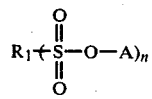

wherein $R_1$ may be any n-valent group; A represents a group of atoms that are bound to the oxygen atom in the formula (I) through a nitrogen atom; and n is an integer of from 1 to 4.

6. The photographic material of claim 1, wherein the carboxylic acid activating condensing agent is a compound of the formula (II):

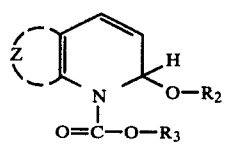

wherein $R_2$ is an aliphatic group; $R_3$ is an aliphatic group or an aryl group and the carboxylic acid residue of the formula $R_3$—O—CO— in the formula (II) is such that when it reacts with the carboxylic acid group of gelatin to form a mixed acid anhydride, the electron density on the carbonyl carbon is lower than that of the carboxylic acid group in gelatin; Z represents a group of atoms necessary to form a benzene nucleus.

7. The photographic material of claim 1, wherein the activating condensing agent is a compound of the formula (III):

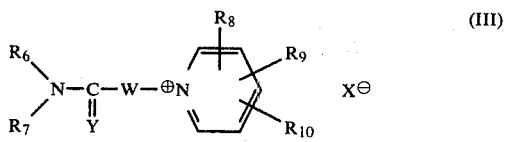

wherein $R_6$ and $R_7$ are independently an alkyl, allyl or aralkyl group and $R_6$ and $R_7$ may combine to form 5- or 6-membered ring which may contain 1 to 2 hetero atoms other than the nitrogen atom to which $R_6$ and $R_7$ are bound; Y is an oxygen atom or sulfur atom; W is an oxygen atom or is a single bond; $R_8$, $R_9$ and $R_{10}$ are independently a hydrogen atom, an alkyl group of up to 5 carbon atoms, an alkoxy group of up to 4 carbon atoms, an acrylamido group of up to 4 carbon atoms, and a carbamoyl group; $X^\ominus$ is an organic or inorganic acid anion, and $X^\ominus$ is absent from the formula (III) when any of $R_6$, $R_7$, Y, $R_8$, $R_9$ and $R_{10}$ includes a sulfonate anion.

8. The photographic material of claim 1, wherein the antistatic layer contains about 0.01 to 50 millimols of the carboxylic acid activating condensing agent per mol of the carboxyl group of the polymer.

9. The photographic material of claim 6, wherein the antistatic layer contains about 0.5 to 20 millimols of the carboxylic acid activating condensing agent per mol of the carboxyl group of the polymer.

10. The photographic material of claim 1, wherein the antistatic layer forms the back layer or a surface protective layer for the back layer.

11. The photographic material of claim 1, wherein the antistatic layer forms a surface protective layer.

12. The photographic material of claim 7, wherein Y is an oxygen atom.

13. The photographic material of claim 1, wherein 5 to 60 mol% of the carboxylic acid groups in said polymer are neutralized.

14. The photographic material of claim 1, wherein said antistatic layer contains a matting agent, a lubricant, a surfactant, colloidal silica, or a gelatin cross-linking agent.

* * * * *